United States Patent
Barfuss et al.

(10) Patent No.: US 7,508,388 B2
(45) Date of Patent: Mar. 24, 2009

(54) METHOD FOR EXTENDING THE DISPLAY OF A 2D IMAGE OF AN OBJECT REGION

(75) Inventors: Helmut Barfuss, Erlangen (DE); Karl Barth, Höchstadt (DE); Gerd Wessels, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 105 days.

(21) Appl. No.: 11/438,029

(22) Filed: May 19, 2006

(65) Prior Publication Data

US 2006/0262118 A1 Nov. 23, 2006

(30) Foreign Application Priority Data

May 19, 2005 (DE) .................. 10 2005 023 194

(51) Int. Cl.
*G06T 15/00* (2006.01)
(52) U.S. Cl. .................. 345/418; 345/428; 345/629; 703/11; 600/407; 600/427
(58) Field of Classification Search .................. 345/418, 345/629, 428, 426; 703/11; 600/407, 425
See application file for complete search history.

(56) References Cited

U.S. PATENT DOCUMENTS

| | | | |
|---|---|---|---|
| 5,987,345 A | * | 11/1999 | Engelmann et al. ......... 600/407 |
| 6,078,349 A | | 6/2000 | Molloy ........................ 348/15 |

(Continued)

FOREIGN PATENT DOCUMENTS

DE 101 51 438 A1 1/2003

(Continued)

OTHER PUBLICATIONS

Hahn et al., Visualization and Interaction Techniques for the Exploration of Vascular Structures, Center for Medical Diagnostic system and Visualization, Bremen, Germany, pp. 395-402, 2004.*

(Continued)

*Primary Examiner*—Phu K Nguyen
(74) *Attorney, Agent, or Firm*—Schiff Hardin LLP

(57) ABSTRACT

In a method to extend the display range of 2D image recordings of an object region, particularly in medical applications, first 2D or 3D image data are acquired from a larger object region, and at least one additional set for 2D image data of a smaller object region is acquired that lies within the larger object region The first 2D or 3D image data are brought into registration with the additional 2D image data with a projection geometry. From the first 2D or 3D image data, an image data set is generated for an image display of the first object region, which is suitable for combination with the additional 2D image data. In the image display of the larger object region, at least temporarily, at least one display of the additional 2D image data is integrated, by image data in the first image data set, for the image display of the larger object region, being replaced with image data from the additional 2D image data representing the smaller image region. An overview of the larger object region is thus enabled, with the smaller object region of interest being displayed within the image in a more up-to-date fashion, as well as with higher resolution and/or higher contrast.

18 Claims, 2 Drawing Sheets

U.S. PATENT DOCUMENTS

| | | | |
|---|---|---|---|
| 6,630,937 B2* | 10/2003 | Kallergi et al. | 345/619 |
| 7,191,110 B1* | 3/2007 | Charbel et al. | 703/11 |
| 7,311,705 B2* | 12/2007 | Sra | 606/41 |
| 2003/0181809 A1* | 9/2003 | Hall et al. | 600/425 |

FOREIGN PATENT DOCUMENTS

| EP | 10 056 049 A2 | 11/2000 |
|---|---|---|

OTHER PUBLICATIONS

Brown, A Survey of Image Registration Techniques, ACM Computing Surveys, Dec. 1992, pp. 325-376.*

"Super-Resolution Imaging: Use of Zoom as a Cue," Joshi et al, Image and Vision Computing, vol. 22 (2004) pp. 1185-1196.

"Multi-Modality Gaze-Contingent Displays for Image Fusion," Nikolov et al, Proc. Of the 5th Int. Conf. on Information Fusion, vol. 2 (2002) pp. 1213-1220.

"Merging Virtual Objects with the Real Word: Seeing Ultrasound Imagery within the Patient," Bajura et al., Computer Graphics, vol. 26, Jul. 2, 1982, pp. 203-210.

"Two-Level Volume Rendering—Fusing MIP and DVR," Mroz et al., IEEE Visualization (2000) pp. 211-218.

"Volumetric Rendering of Multimodality, Multivariable Medical Imaging Data," Tan et al., Symposium on Volume Visualization (1989), pp. 45-50.

* cited by examiner

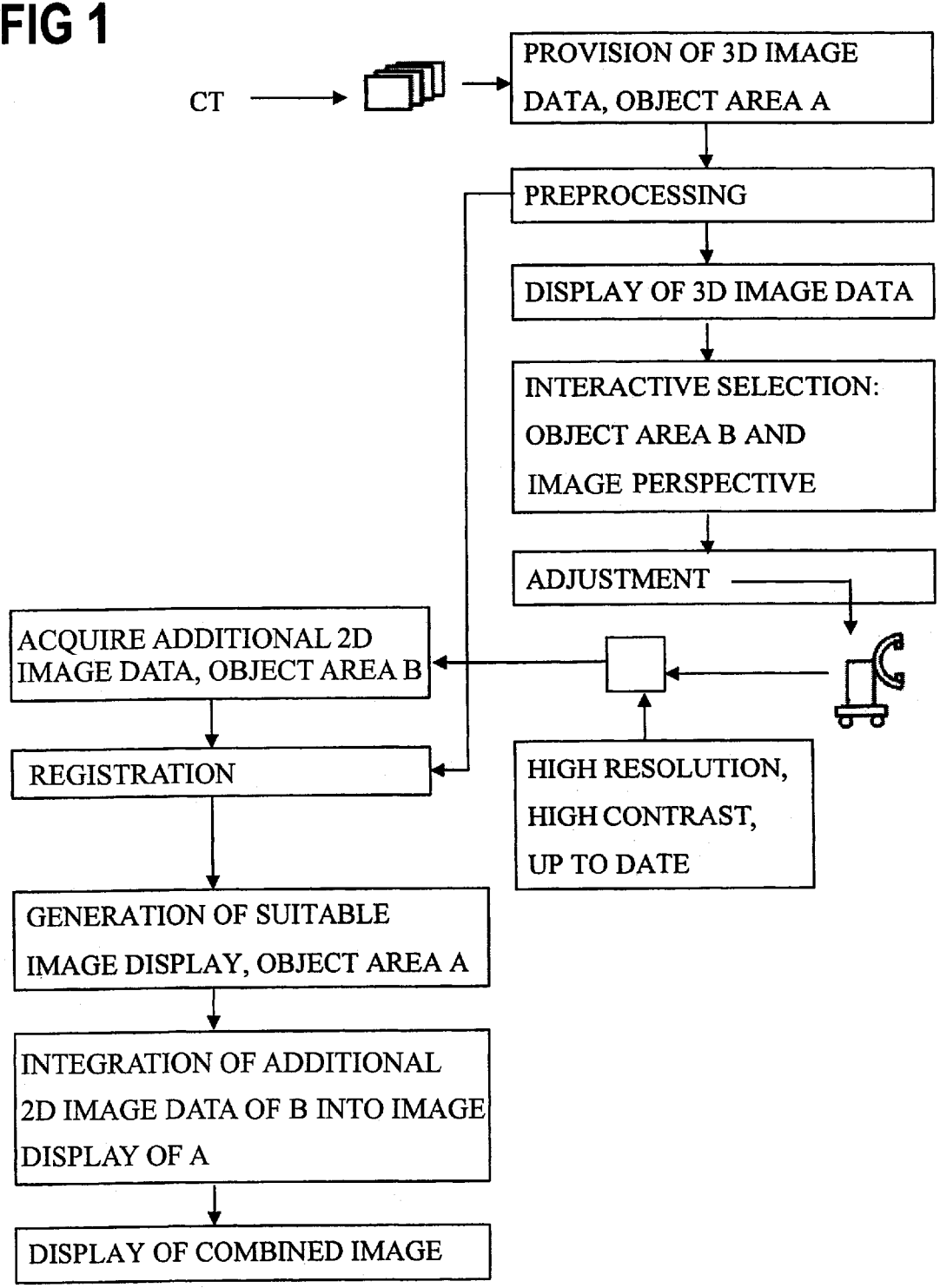

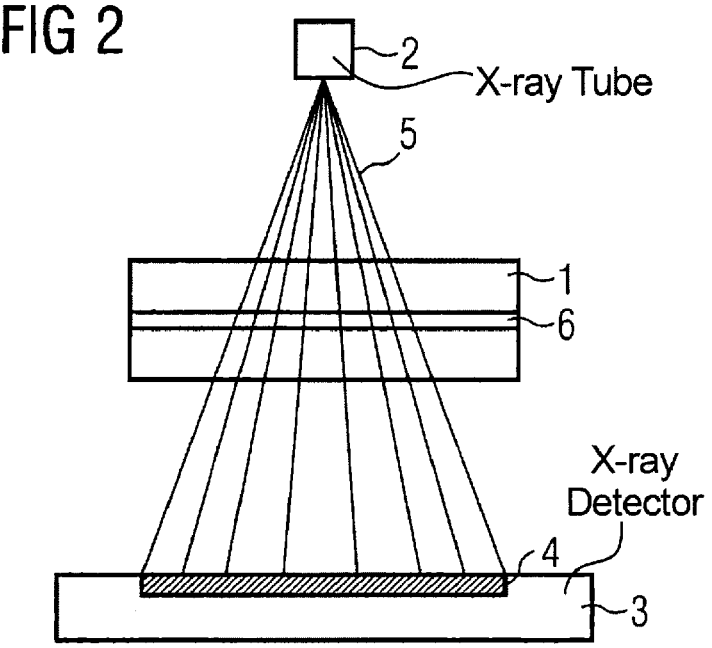
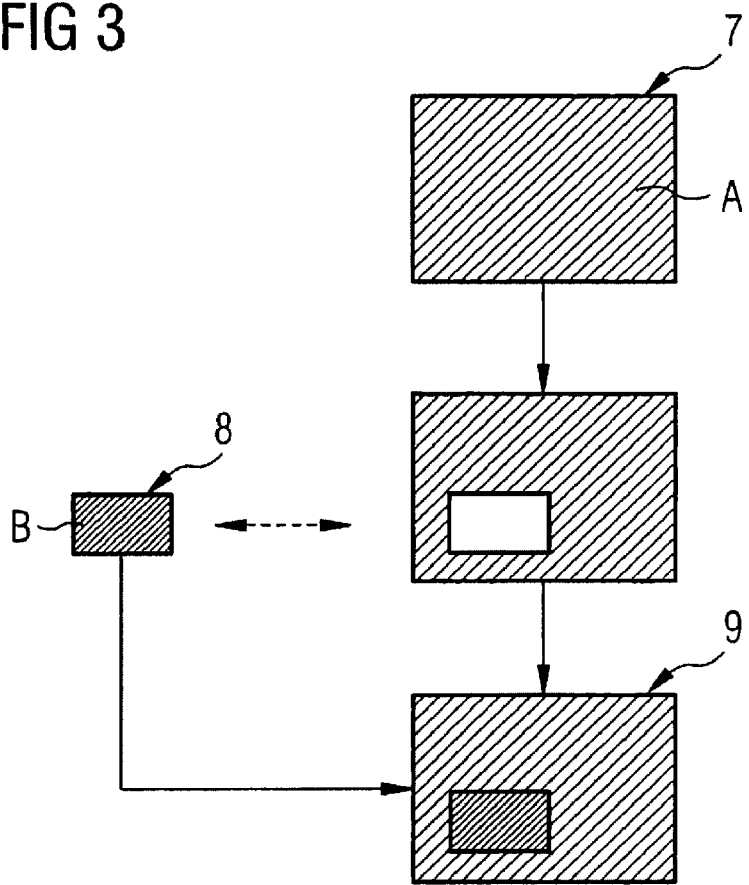

METHOD FOR EXTENDING THE DISPLAY OF A 2D IMAGE OF AN OBJECT REGION

BACKGROUND OF THE INVENTION

1. Field of the Invention

The present invention concerns a method for the extension of the display range of 2D images of an object region of the type wherein first 2D or 3D image data of a larger object region are provided, at least one set of additional 2D image data of a smaller object region is obtained that lies within the larger object region, and the additional image data are displayed in combination with the 2D image.

2. Description of the Prior Art

In surgical interventions nowadays, compact image capture systems such as mobile X-ray devices, ultrasound devices, or endoscopes/laparoscopes are often used. These modalities, however, offer only a limited field of view for image capture. For the surgeon, however, it is desirable to be able to view the local situation in the treatment area in a larger context as well.

Different options are known in which 3D image data of the body are recorded at some larger time previous to the surgical intervention, for instance using X-rays, X-ray computed tomography, or magnetic resonance tomography, in order to be able to visualize the spatial context during the intervention using this 3D image data. A distinction can be made between two variants. In the first variant, a current local display of the treatment area, which has been recorded with the mobile image capture modality, appears on a main monitor. On a second monitor, for comparison, there appears the overall view from the previously recorded 3D image data. In the second variant, there is a superimposition or merging of images. The current local view, for instance an endoscope view, is directly superimposed on the overall view from the earlier examination. Both views can be appropriately transparent and shown in complementary colors. An example of such a variant is described in DE 102 10 646 A1, which describes a superimposition of image data from a 3D image capture modality onto the 2D fluoroscopic imaging of the examination region. The projection geometry of the 2D fluoroscopic image is taken into account in the superimposition, just as in another embodiment of the process the depth from which the structures detectable primarily in the 2D fluoroscopic image originate is also taken into account.

SUMMARY OF THE INVENTION

An object of the present invention is to provide a method for extension of the display range of 2D image recordings of an object area which offers advantages precisely when using mobile compact devices for the capture of 2D image recordings.

In accordance with the present invention, first 2D or 3D image data are provided for a larger object area or region, the first data preferably having been acquired previously with an imaging tomographic modality. At least an additional set of 2D image data of a smaller object area or region is obtained that lies within the larger object area, and the first 2D or 3D image data are brought into registration with the projection geometry of the additional 2D image data. The acquisition of the additional 2D image data preferably is performed with a mobile compact device which has only a limited field of view for image capture. This type of compact device, for instance, can be a mobile X-ray C-arm device or an endoscope. From the first 2D or 3D image data, an image data set is generated for an image display of the larger object area that is suitable for combination with the additional 2D image data, i.e., with the same scaling and perspective. In this image display of the larger object area of the first 2D or 3D image data, at least temporarily, a display of the additional 2D image data are integrated, by replacing image data in the first image data set for the image display of the larger object area representing the smaller object area, with image data of the additional set of 2D image data, so that a synthetic image data set results and is displayed.

In the inventive method, therefore, the inventively recorded additional 2D image of the local object area, with the advantages of being up to date, as well as the possibility of higher resolution and a full contrast, is integrated into a first overall image which does include a larger object area, but has an older date of recording and may have a lower resolution and/or a lower contrast. This is used to extend the displayable object area using the inventive process. Furthermore, in case of suitable performance of the additional 2D image data, the smaller object area recorded can be displayed with a higher resolution and/or a higher contrast. This smaller object area is called the core area or core image below, and complete overall display is called a context image.

In a preferred embodiment of the inventive method, the additional 2D image data are therefore also acquired with a higher resolution than the first 2D or 3D image data. The image display of the larger object area thus is adapted to the higher resolution of the integrated display of the additional 2D image data by interpolation. In another embodiment, the additional 2D image data are also acquired with a higher image contrast or with different characteristics (e.g. by using tracers or contrast substances) than the first 2D or 3D image data. This leads to a locally better and more current detail display in a limited area of the combined image display. The synthesis of the two images is performed based on a correct location and orientation indexing, as well as preferably with a calibration during the 2D recording.

An advantage of the inventive method is that the display of the additional 2D image data is integrated into the first image display of the larger object area by substitution of the existing image data. From the suitably adapted first image display of the larger object area, the smaller object area is excised for this purpose and replaced with the image data of the additional 2D image data. Image superposition, as is conventional does not take place. Of course, such an image superposition could be provided as an additional option for the user.

If the additional 2D image data of the smaller object area are acquired using an X-ray device, then a two-dimensional image results that is composed of a central perspective superimposition of all depth areas in the object. For such an image, a correct scaling in comparison to a 3D image data set of the larger object area is not directly possible, as is necessary for the conventional combination of image recordings. The scale of the context image, for instance a 3D image data set from a CT volume capture, is generally known. For the scaling of this type of 3D image data set in comparison with an additional 2D image data, for example, the following two process variations can be used.

For instance, in a first variant at least three spatially uniquely identifiable marks can be attached to the patient that remain on the patient for both the first earlier recording of the 3D image data set as well as for the later additional 2D image data. To increase accuracy and reliability of identification of each mark, more than three marks can be used. The marks can be used for image registration of the current patient position with respect to the earlier recorded first 3D data set. Moreover, from the position detectable in the 2D image data, the image perspective relative to the first 3D image data set is determined with which the additional 2D image data was obtained. Knowledge of this image (data acquisition) perspective or projection geometry of the additional 2D image data enables the calculation, in combination with the registration of the first 3D image data set, of an image display of the larger image area through superimposition of the different irradiated layers according to this perspective, so that a correct combination of the two images is possible.

In a second exemplary variant, registration of the patient with respect to the device structure for the operation, for instance relative to a patient bed, and the recording of the position and orientation of the imaging system for the additional 2D image data for the core image, for instance of the C arm for a C arm device, relative to the patient bed. From the knowledge of these parameters as well, the projection geometry can be calculated and used for the matching display of the core image and the context image. The knowledge of the position and orientation of the patient relative to the image capture modality for the creation of the context image is assumed. Of course, different registration or indexing technologies are also possible in order to enable as exact as possible a combination of displays of the larger and smaller object areas, for instance using a navigation system which calculates the geometric relationship between the patient and the devices and continually tracks it. The angle and distance sensors available on C-arm devices can also be used for indexing.

The inventive method is particularly suitable for mobile X-ray image capture, for instance using a mobile C-arm device. Such a device can be brought from a standby position to the operation table very quickly, with the coupling through the C-arm, the X-ray source and the X-ray detector being optimally adjusted at all times. In the later part of the intervention, such a device can often remain on site, since the relatively large opening of the C-arm generally leaves access to the patient open for the physician. The disadvantage of the use of such a mobile X-ray device, is that due to the compactness required, only a relatively small image area is recorded. Extensive body structures are cut off from the edges of the image display. This is the disadvantage that can be avoided with the inventive process by extending the display context.

In an embodiment of the inventive method, the first 3D image data is not used to calculate a superimposition of all irradiated layers in central projection, but rather the depth range is calculated and excised that includes significant structures shown in the additional 2D image data. The fact that the structures of interest in the additional 2D image data often lie at a certain depth in the object is used advantage. The corresponding depth range is therefore, in this embodiment, excised from the first 3D image data and used as an image display particularly in the form of a cross-section or layer package image of the larger object area, in which the additional 2D image data has been integrated. In an embodiment, the first 3D image data of the context image are previously depth-encoded to assist the selection of depth. Due to this depth encoding, the depth selection can be performed particularly quickly, for instance with hardware support and/or using a lookup table in which the encoding of the different depth ranges is assigned.

In another embodiment of the inventive method, the first 2D or 3D image data are also preprocessed for generation of the image display to be combined such that only structure of the larger object area are present in the image display, or at least highlighted, that are of interest to the user in the current application. For instance, the first 2D or 3D image data can represent recordings of the larger object area obtained by subtraction angiography, if only the tissue structures are of interest for the current application and, for instance, the additional core image is also obtained by subtraction angiography.

In the inventive method, it is of course also possible to integrate multiple additional sets of 2D image data of different smaller object areas into a suitable overall display from the first 2D or 3D image data provided. A switch between the display of different core areas is also possible. In a further embodiment, different image displays of the respective additional sets of 2D image data, for instance with different contrast or after use of filters to highlight different structures in different color codings, can also be combined with the first display of the larger object area. Here as well, a switch between the different displays is possible. Furthermore, a superimposition of the different displays of the core area can be performed, then preferably the transparency or the brightness of the different superimposed displays can be continuously changed by the user.

Furthermore, in the inventive method when using distorting capture devices, for instance endoscopes or X-ray systems with telescopic lenses or image amplifier tubes, distortion corrections are made to the image data or to the additional 2D image data and, if necessary, that is if it is distorted, to the first 2D image data, so that virtually distortion-free images are used for the combination of the image displays.

The different embodiments of the process of course can be combined. Furthermore, it should be noted that although embodiments of the inventive method are explained in the context of image processing in a medical applications, but they can also be used in non-medical application areas with different objects. If, instead of the first 3D image data, first 2D image data are provided, the parts of the calculations of a suitable image display from the context image data may be omitted. The first 2D image data must in this case already be recorded using an imaging perspective approximately identical to that used to record the additional 2D image data.

The inventive method can also be used for the adjustment of the modality used for the additional 2D image data, to focus the recording system or the recording lens optimally on the desired core area. For this purpose, before the acquisition of the additional 2D image data of the smaller object area, an image of the larger object area is generated from the first 2D or 3D image data and displayed for the user. The user then has the option of interactive determination of the smaller object area for the additional 2D image data, with the data being collected for the object area determined and used for the automatic adjustment of the capture device for the capture of the additional 2D image data. Registration of the first 2D or 3D image data with this recording device must previously be performed, for instance using marks attached to the patient and a navigation device coupled to the capture device with which the marks can be targeted. In a further version of this embodiment, the image of the larger object area can be suitably enlarged or reduced by the user, rotated in three dimensions, and translated, interactively on the screen in each case, in order also to determine the viewing perspective for the additional 2D image data. This perspective is also recorded and used for the automatic adjustment of the capture device.

DESCRIPTION OF THE DRAWINGS

FIG. 1 is a flowchart of an embodiment of the inventive method.

FIG. 2 shows the relationships of the components for an additional 2D X-ray data acquisition.

FIG. 3 schematically shows the integration of the additional 2D image data into the image display of a larger object area.

DESCRIPTION OF THE PREFERRED EMBODIMENTS

The inventive method is explained in detail using the example of an operation, for instance after a pelvic fracture, in which during the operation additional 2D X-ray data of the treatment area are obtained using a mobile C-arm device and displayed.

Both for the planning and for the performance of an operation nowadays, a series of first 3D image data sets are used which are obtained before the intervention, for example from CT volume recordings. Through visualization of this first 3D image data, a complete, large-scale overview is obtained of the entire relevant body environment. In an operation, the physician must rely on a current image exposure for different reasons, which is executed for instance using endoscopy, X-ray illumination, or with radiographical individual recordings. In the case of repeated additional image exposures during the operation, the physician can track changes immediately in this manner. The current image exposure is already required for safety, since changes in the anatomy may have occurred since the pre-examination, for instance due to the movement of soft tissue structures. Furthermore the additional current local image captures can often be performed with a higher image quality, since the recording parameters can be adjusted for higher resolution and specially optimized contrast.

In the present example, as an imaging X-ray system during the operation, a mobile X-ray C-arm device is used. Such a device is easily handled and offers at least a limited access to the patient on the operating table.

Due to the compactness of such a mobile X-ray C-arm device, it spans a smaller image area than most stationary devices. In the additional 2D image data acquired during the operation, therefore, extended body structures are cut off from the edges of the additional 2D image data. To improve the display, this limited display area is enlarged by using the inventive method.

To do this, before the operational intervention, a pre-examination is performed in which first 3D image data of a larger object area A of the patient are recorded using a volume recording and provided. This first 3D image data is recorded in the inventive method using an X-ray CT device, but also can be obtained using other image-capturing tomographic modalities, for instance an MRI system. When acquiring the additional 2D image data of the smaller object area B during the operation, the geometrical display parameters of these 2D image data are also recorded, so that with a registration of the patient position relative to the C-arm device used during the operation and relative to the preoperative volume recording, the geometrical mapping of all image data sets can be determined. For such a registration, the devices, both the CT device and the C-arm device, are principally set up. Both modalities used in the example usually generate volume data sets or can generate such data sets, which include a scale according to the DICOM standard, so that the scaling can also be matched.

In the current example, during the operation after a pelvic fracture in which fixing with a plate is planned, the previously obtained first volume image of the larger object area A is provided at a suitable point in time. A registration can be performed, for instance using marks which are attached to the patient during the volume recording. By comparing the marks detectable in the first volume recording with the marks remaining on the patient immediately before execution of the operation, for instance by moving to the marks using a navigation system, such a comparison can be performed. The navigation system also establishes the relationship to the data acquisition system of the C-arm device.

In the current example, the first volume image of the larger object area A is visualized on a screen. The physician now has the option of moving this display in three dimensions, to rotate it, and to zoom it. This is done using familiar interactive processing tools. The area around the fracture is now centered in this display, and zoomed out, but the physician would like to see it at a higher resolution and with the current recording date. It is also possible to filter and display the first volume data of the larger object area A in such a way that they approximate the additional detail for the core area. This previously simulated core image can be virtually rotated and translated in three dimensions on the monitor. In an optimal orientation, the virtual 3D coordinates are recorded and used to adjust the mobile C-arm device for the core area. Now this mobile C-arm device is locally used with this adjustment at its highest resolution and optimum contrast to record an additional two-dimensional image (core image) of the current position of the bone pieces and, for example, partially inserted screws.

From the previously recorded first 3D image data set, an image display is then generated, which has the same perspective and scaling as the additional 2D image recording of the fracture. This can be derived based on the determined or calculated data for position and orientation of the additional 2D image data or from the resulting perspective.

FIG. 2 schematically shows the relationships in such a 2D X-ray data acquisition of an object 1. The projection geometry of this image data acquisition is shown by the X-ray beams 5, indicated in FIG. 2 between the X-ray tube 2 and X-ray detector 3. In the image extent 4 of such a 2D X-ray image, all structures lying on the path of the individual X-ray beams 5 through the object 1 are projected onto each other with different imaging scales. When generating a suitable image display from the first 3D image data set, therefore, this central projection must be taken into account. The larger object area of object 1 can be obtained in the same way using central perspective superimposition of the different layers present in the first 3D image data set. In a further alternative, in which the interesting structures in the first 2D image acquisition occur only in a certain depth range 6 of object 1, exactly this depth range 6 can be excised from the first 3D image data set, for instance using clipping, and used as an image display of the larger object area A.

FIG. 3, shows an example of the combination of the image 8 produced with the additional 2D image data with the image display 7 of the larger object area A. In image display 7 of this larger object area A, the image data that represent the smaller object area B are cut out and replaced with the image data from the additional 2D image recording 8 which is available in the current example with a higher resolution and improved contrast. The combined image 9 is then displayed for the physician on a monitor. The entire process as it has been explained in the current example, is shown in the flow chart in FIG. 1.

Of course, the 2D image 8 or a display of the first 3D image data set, or the image display 7 obtained therefrom can also continue to be displayed separately for the combination with the additional 2D image 8. Furthermore, it is advantageous to provide a switching function which can be used to switch back and forth between the display of the core area from the pre-examination and the current high-resolution core image in the combined image display. A transparent superimposition of one or more currently generated core images onto the image display of the larger object area A can additionally be provided, with the superimposition limited to the coverage range of the core image.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for extending a display range of a 2D image of an object region, comprising the steps of:
   providing multi-dimensional image data from a larger object area of a subject to a processor;
   acquiring at least one additional set of 2D image data from only a smaller object area, within said larger object area by exposing said subject to a data acquisition procedure in which 2D image data are acquired only from said smaller object area, and providing said at least one additional set of 2D image data to said processor;
   in said processor, bringing said multi-dimensional image data into registration with said additional set of 2D image data using a projection geometry;
   displaying an image of the larger object area represented by the multi-dimensional image data at an image display; and
   within the display of the larger object area at said image display, said processor causing at least temporary display of a 2D image represented by said additional set of 2D image data, by replacing image data in said multi-dimensional image data, which represent said smaller image area, with image data from said additional set of 2D image data.

2. A method as claimed in claim 1 comprising acquiring said at least one additional set of 2D image data with a higher resolution than said multi-dimensional image data, and adapting the display of the image of the larger image area at said image display to the higher resolution of said additional set of 2D image data by interpolation of said multi-dimensional image data.

3. A method as claimed in claim 1 comprising acquiring said at least one additional set of 2D image data so that the image represented by said one additional set of 2D image data has at least one different image characteristic, other than a size of said object area, from said image represented by said multi-dimensional image data.

4. A method as claimed in claim 1 comprising acquiring said multi-dimensional image data as 3D image data with a tomographical data acquisition modality.

5. A method as claimed in claim 1 wherein said multi-dimensional image data are 2D image data, and comprising acquiring said 2D image data and said at least one set of additional 2D image data with an X-ray device.

6. A method as claimed in claim 1 wherein said multi-dimensional image data are 2D image data, and comprising acquiring said 2D image data with an imaging modality selected from the group consisting of an endoscope, a laparoscope, a two-dimensional ultrasound apparatus, and a two-dimensional camera.

7. A method as claimed in claim 1 comprising acquiring said at least one additional set of 2D image data as a time sequence in a cine mode with an imaging modality selected from the group consisting of an endoscope, a laparoscope, a two-dimensional ultrasound apparatus, and a two-dimensional camera.

8. A method as claimed in claim 1 wherein said projection geometry is a projection geometry of said at least one additional 2D image data set, and wherein the step of integrating said image of said image of said larger object area with said image of said smaller object area at said image display comprises displaying said image of said larger object area at said image display as an image created by operating on said multi-dimensional image data with the projection geometry of said at least one additional set of 2D image data.

9. A method as claimed in claim 1 comprising automatically electronically determining a depth range within said multi-dimensional image data containing structures also contained in said at least one additional set of 2D image data, and excising image data in said multi-dimensional image data representing said depth range in said larger object area and replacing data in the excised data, which represent said smaller image area, with said at least one additional set of 2D image data in the image of the larger object area displayed at said image display.

10. A method as claimed in claim 9 comprising indexing said multi-dimensional image data according to depth, and excising said data in said depth range of multi-dimensional image data dependent on said indexing.

11. A method as claimed in claim 1 comprising, before acquiring said at least one additional set of 2D image data, generating an image of said larger object area at said image display from said multi-dimensional image data and allowing manual user interaction, via a control unit that controls acquisition of said at least one additional set of 2D image data, to enter geometrical data into the control unit, dependent on the display of the larger object area, and automatically controlling acquisition of said at least one additional set of 2D image data according to said geometrical data.

12. A method as claimed in claim 11 comprising allowing user interaction to selectively modify the image of the larger image area at said image display by an operation selected from the group consisting of enlargement, rotation and translation, to allow a data acquisition perspective to be selected for said at least one additional set of 2D image data, and allowing user entry of said selected imaging perspective into said control unit and controlling acquisition of said at least one additional set of 2D image data according to the selected imaging perspective.

13. A method as claimed in claim 1 comprising preprocessing said multi-dimensional image data to retain only structures therein that are also of interest in said smaller object area.

14. A method as claimed in claim 1 comprising preprocessing said multi-dimensional image data to highlight only structures therein that are also of interest in said smaller object area.

15. A method as claimed in claim 1 comprising subjecting at least one of said multi-dimensional image data and said at least one set of additional 2D image data to automatic electronic distortion correction before displaying said image of said larger object area and said image of said smaller object area at said image display.

16. A method as claimed in claim 1 comprising at said image display, allowing selective switching between display of said larger object area without said image of said smaller object area integrated therein, and display of said image of said larger object area with said image of said smaller object area integrated therein.

17. A method as claimed in claim 1 comprising allowing selective switching among different versions of said image of said smaller object area integrated in said image of said larger object area, with said image of said smaller object area displayed with respectively different display characteristics.

18. A method as claimed in claim 1 comprising generating said different versions of said display of said smaller image area by superimposing said image of said smaller object area on said image of said larger object area with a selectively selected display characteristic selected from the group consisting of a degree of transparency of said image of said smaller object area and a brightness of said image of said smaller object.

* * * * *